US 6,514,247 B1

(12) United States Patent
McGaffigan et al.

(10) Patent No.: US 6,514,247 B1
(45) Date of Patent: *Feb. 4, 2003

(54) TRANSURETHRAL NEEDLE ABLATION DEVICE WITH ALIGNED HANDLE

(75) Inventors: Thomas H. McGaffigan, Saratoga, CA (US); Christopher S. Jones, Palo Alto, CA (US)

(73) Assignee: Vidamed, Inc., Minneapolis, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/416,206

(22) Filed: Oct. 8, 1999

Related U.S. Application Data

(63) Continuation of application No. 08/833,984, filed on Apr. 11, 1997, now Pat. No. 5,964,756.

(51) Int. Cl.[7] ................................................ A61B 18/18
(52) U.S. Cl. ............................ 606/41; 606/47; 607/101
(58) Field of Search ............................. 606/41, 46, 47, 606/49; 607/101, 102; 604/21, 22

(56) References Cited

U.S. PATENT DOCUMENTS

| 2,008,526 A | 7/1935 | Wappler et al. |
| 2,038,393 A | 4/1936 | Wappler |
| 4,016,886 A | 4/1977 | Doss et al. |
| 4,474,174 A | 10/1984 | Petruzzi |
| 4,524,770 A | 6/1985 | Orandi |

(List continued on next page.)

FOREIGN PATENT DOCUMENTS

WO     WO 96/32896     10/1996

OTHER PUBLICATIONS

Greenwald Surgical Company, Inc., "Orandi Resectoscope Injection Needle for Injection of Local Anesthetics," (Undated) Sheet No. P000121.
E.F. Nation, M.D., "Evolution of Knife–Punch Resectoscope," (Apr. 1976) Urology, vol. VII, No. 4, pp. 417–427.
R. Gutierrez, "Transurethral Treatment of Bladder Neck Obstructions: Endoscopic Prostatic Resection," (Apr. 1933) History of Urology, vol. II, Chapter V, pp. 137–186.
C.W. Ogden, Heat and the Prostate from Electrolysis to Microwaves: Lessons from an Historical Perspective, (Undated) Abstract, 2 sheets, p. 366.
Graversen, et al., "Transurethral incisions of the prostate under local anaesthesia in high–risk patients: a pilot study," (1987) Abstract, HealthGate Home Page, p. P000115.
Miller, et al., "Integrated cystoscope: first rigid multipurpose operating cystoscope for local anesthetic endoscopy," (1989) Abstract, HealthGate Home Page, p. P000116.

(List continued on next page.)

Primary Examiner—Michael Peffley
(74) Attorney, Agent, or Firm—Dorsey & Whitney LLP

(57) ABSTRACT

A transurethral needle ablation device for use by a human hand to treat the prostate of a human male. The device includes a cartridge assembly having an elongate probe member and a stylet. The elongate probe member has proximal and distal extremities and is provided with a passageway extending from the proximal extremity to the distal extremity. The stylet is slidably mounted in the passageway of the elongate probe member. A housing is included in the device. The cartridge assembly is removably mountable on the housing. An assembly adapted for actuation by the human hand is carried by the housing and coupled to the proximal extremity of the stylet for causing the distal extremity of the stylet to extend into the tissue of the prostate.

18 Claims, 7 Drawing Sheets

U.S. PATENT DOCUMENTS

| | | | |
|---|---|---|---|
| 5,238,461 A | | 8/1993 | Gotman .................... 475/248 |
| 5,282,800 A | | 2/1994 | Foshee et al. ............... 606/52 |
| 5,370,675 A | * | 12/1994 | Edwards et al. ........... 607/101 |
| 5,409,453 A | | 4/1995 | Lundquist et al. |
| 5,456,689 A | * | 10/1995 | Kresch et al. ............. 606/180 |
| 5,520,684 A | | 5/1996 | Imran ........................ 606/41 |
| 5,549,644 A | | 8/1996 | Lundquist et al. |
| 5,667,488 A | * | 9/1997 | Lundquist et al. ........... 604/22 |
| 5,672,171 A | | 9/1997 | Andrus et al. ............... 606/15 |
| 5,749,846 A | * | 5/1998 | Edwards et al. ............. 604/22 |
| 5,849,011 A | * | 12/1998 | Jones et al. .................. 606/47 |
| 5,928,255 A | * | 7/1999 | Meade et al. .............. 606/170 |
| 5,964,756 A | * | 10/1999 | McGaffigan et al. ......... 606/41 |

OTHER PUBLICATIONS

Orandi, "Urological endoscopic surgery under local anesthesia: a cost–reducing idea," (1984) Abstract, HealthGate Home Page, p. P000117.

Orandi, "Transurethral resection versus transurethral incision of the prostate," (1990) Abstract, HealthGate Home Page, p. P000118.

H. LeVeen, "Method for treating benign and malignant tumors utilizing radio frequency," (Nov. 16, 1976) Abstract, USPTO.GOV, U.S. Patent No. 3,991,770, pp. P000119–P000120.

R. Auhll, "The Use of the Resectoscope in Gynecology," (Oct. 1990) Biomedical Business International, pp. 91–99.

L. Geddes, "A Short History of the Electrical Stimulation of Excitable Tissue Including Electrotherapeutic Applications," (1984) A Supplement to The Physiologist, vol. 27, No. 1, pp. P000066–P000071.

W. Moseley, M.D., "The History of Treatment of BPH Including Current Treatment Alternatives," (Undated) pp. P000187–P000190.

D. Paulson, M.D., "Diseases of the Prostate," (1989) Clinical Symposia, vol. 41, No. 1., pp. P000191–P000195.

T. Kirwin, "The Treatment of Prostatic Hypertrophy by a new 'Shrinkage' Method," (Aug. 1934) J. Urology, pp. 481–494.

\* cited by examiner

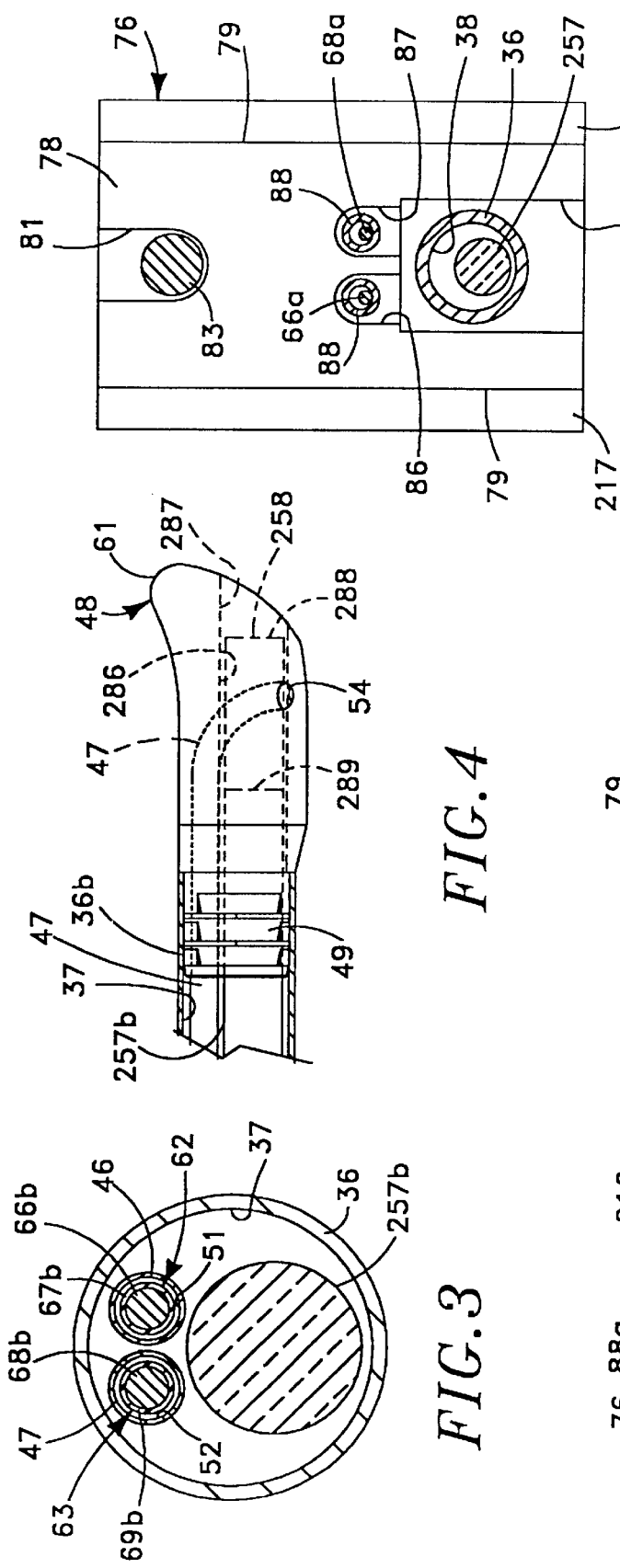
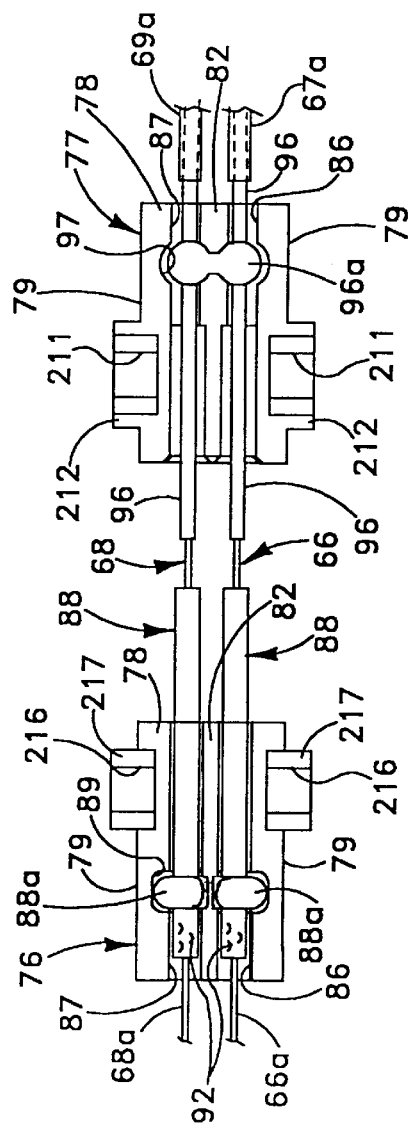
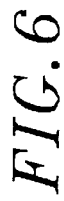

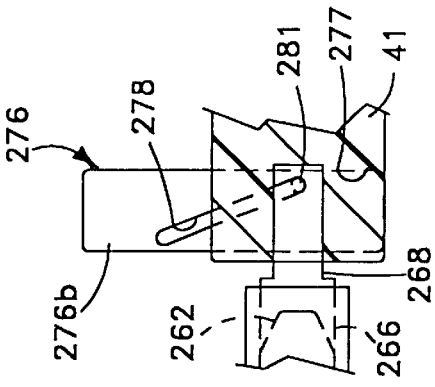
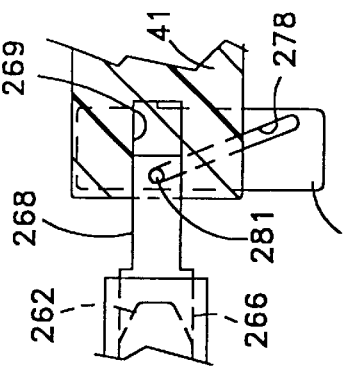
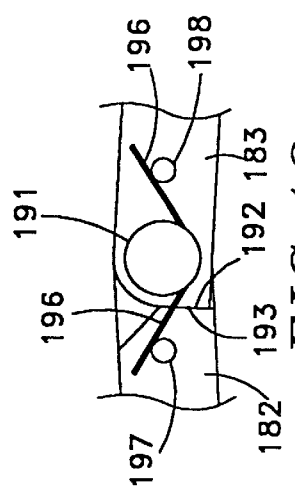
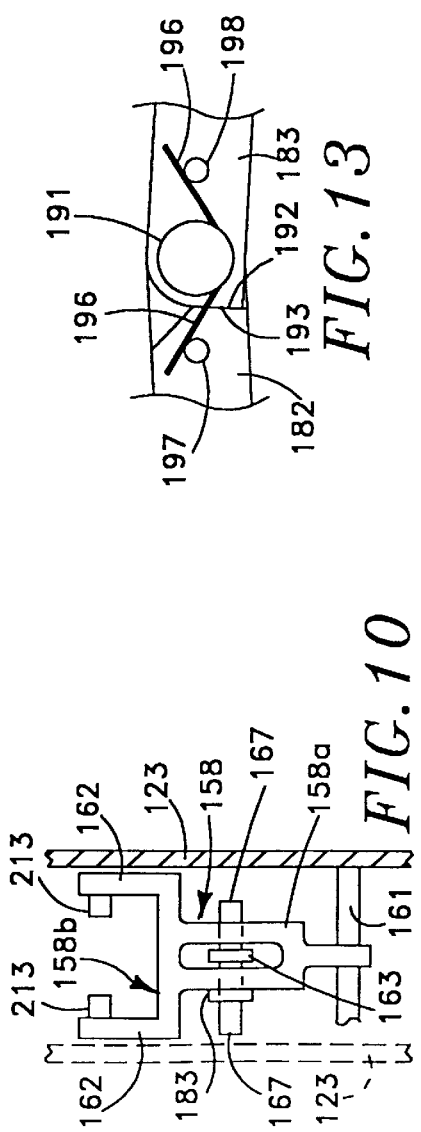
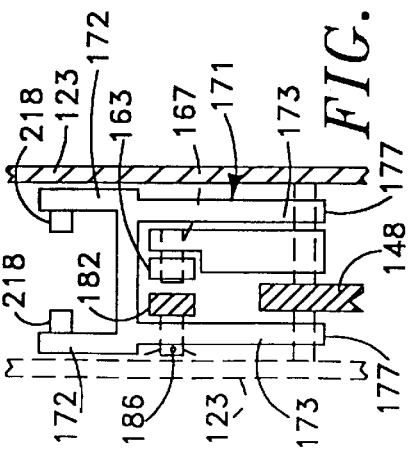
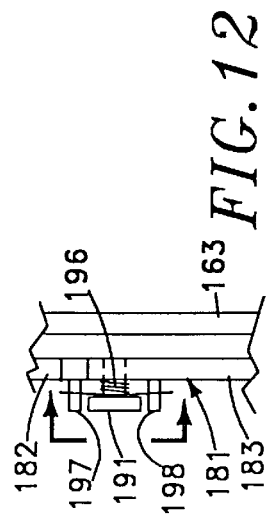

TRANSURETHRAL NEEDLE ABLATION DEVICE WITH ALIGNED HANDLE

This application is a continuation of application Ser. No. 08/833,984 filed Apr. 11, 1997, now U.S. Pat. No. 5,964,756.

This invention pertains generally to medical devices and, more particularly, to transurethral needle ablation devices.

Medical devices have been provided for treating benign prostatic hyperplasia by use of radio frequency energy. See, for example, U.S. Pat. Nos. 5,370,675 and 5,549,644. Some of such devices include components which are disposable so as to reduce the cost of the procedure. In this regard, see International Publication No. WO/00049 having an International Publication Date of Jan. 3, 1997. There remains, however, a need for a new and improved transurethral needle ablation device which is relatively simple in construction, easy to use and inexpensive.

In general, it is an object of the present invention to provide a transurethral needle ablation device having a reusable handle assembly for controlling the deployment of one or more stylets.

Another object of the invention is to provide a device of the above character in which the stylet is contained in a cartridge which can be removably mounted on the handle assembly.

Another object of the invention is to provide a device of the above character in which the stylet includes a radio frequency electrode and an insulating sleeve coaxially disposed about the radio frequency electrode.

Another object of the invention is to provide a device of the above character in which the cartridge permits a scope to be removably coupled thereto.

Another object of the invention is to provide a device of the above character in which the scope can be moved longitudinally between a forward position for viewing distally of the device during its introduction into the body and a rearward position for viewing the stylet as it is deployed from the device.

Another object of the invention is to provide a device of the above character in which the handle assembly has relatively few parts.

Another object of the invention is to provide a device of the above character in which the deployment components of the handle assembly are constantly engaged to ensure proper deployment and retraction of the stylet during the procedure.

Another object of the invention is to provide a device of the above character in which the deployment components of the handle assembly include a planetary gear assembly.

Additional objects and features of the invention will appear from the following description from which the preferred embodiments are set forth in detail in conjunction with the accompanying drawings.

FIG. 3 is a cross-sectional view of the transurethral needle ablation device of FIG. 1 taken along the line 3—3 of FIG. 2.

FIG. 4 is an enlarged side elevation view of the transurethral needle ablation device of FIG. 1 taken along the line 4—4 of FIG. 2.

FIG. 5 is a cross-sectional view of the transurethral needle ablation device of FIG. 1 taken along the line 5—5 of FIG. 2.

FIG. 6 is a cross-sectional view of the transurethral needle ablation device of FIG. 1 taken along the line 6—6 of FIG. 2.

FIG. 10 is a cross-sectional view of the transurethral needle ablation device of FIG. 1 taken along the line 10—10 of FIG. 2.

FIG. 11 is a cross-sectional view of the transurethral needle ablation device of FIG. 1 taken along the line 11—11 of FIG. 2.

FIG. 12 is a top elevational view of the transurethral needle ablation device of FIG. 1 taken along the line 12—12 of FIG. 2.

FIG. 13 is a cross-sectional view of the transurethral needle ablation device of FIG. 1 taken along the line 13—13 of FIG. 12.

FIG. 14 is a cross-sectional view of the transurethral needle ablation device of FIG. 1 taken along the line 14—14 of FIG. 9.

FIG. 15 is a cross-sectional view of the transurethral needle ablation device of FIG. 1 taken along the line 15—15 of FIG. 2.

FIG. 16 is a cross-sectional view of the transurethral needle ablation device of FIG. 1, similar to FIG. 15 and showing the device in another position.

Figure 1:
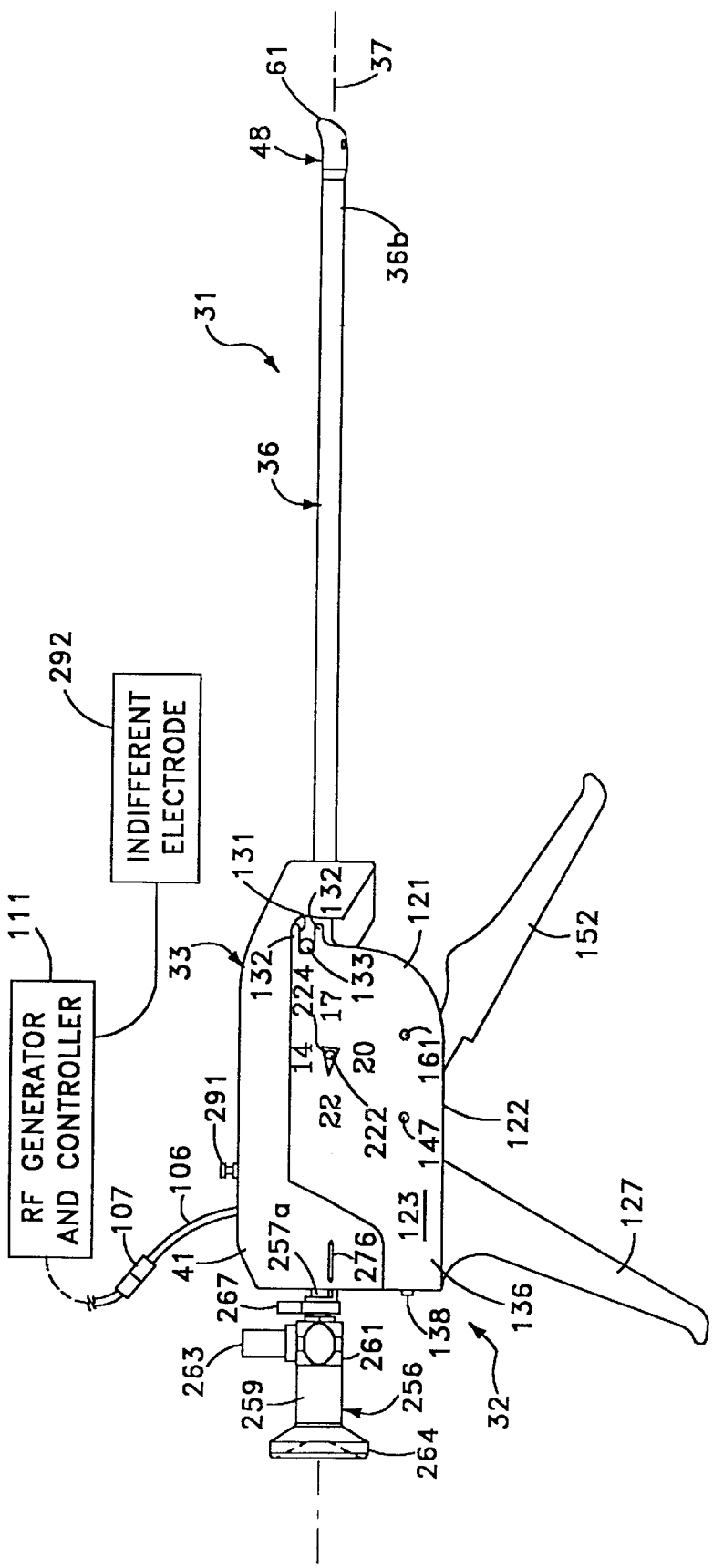
FIG. 1 is a side elevational view of the transurethral needle ablation device with replaceable cartridge of the present invention.

In general, a transurethral needle ablation device for use by a human hand to treat the prostate of a human male is provided. The device includes a cartridge assembly having an elongate probe member and a stylet. The elongate probe member has proximal and distal extremities and is provided with a passageway extending from the proximal extremity to the distal extremity. The stylet is slidably mounted in the passageway of the elongate probe member. A housing is included in the device. Cooperative mating means is carried by the cartridge assembly and the housing for removably mounting the cartridge assembly on the housing. Means adapted for actuation by the human hand is carried by the housing and coupled to the proximal extremity of the stylet for causing the distal extremity of the stylet to extend into the tissue of the prostate.

More in particular, transurethral needle ablation device 31 of the present invention includes reusable handle means in the form of handle assembly 32 and a disposable cartridge assembly or cartridge 33 removably mountable on the handle assembly 32. Cartridge 33 has an elongated member or torque tube 36 made from any suitable material such as stainless steel ( see FIGS. 1, 2 and 7). Torque tube 36 has proximal and distal extremities 36a and 36b and extends along a longitudinal axis 37. Tubular torque tube 36 has a passageway 38 extending longitudinally between its extremities 36a and 36b. The tube 36 is generally circular in cross-section and has an outer diameter of approximately 18.5 French.

A cartridge housing 41 is secured to proximal extremity 36a of torque tube 36. Housing 41 is made from plastic or any other suitable material and has a bore 42 extending longitudinally therethrough. Proximal extremity 36a of torque tube 36 is disposed within bore 42 and secured therein by any suitable means such as an adhesive (not shown). A recess 43 extends upwardly from the bottom of the elongate housing 41. Proximal extremity 36a of torque tube 36 is exposed within the recess 43.

Torque tube 36 extends distally from cartridge housing 41 a distance of approximately 9.5 inches. Accordingly, the torque tube 36 has a length so that when its distal extremity 36b is disposed within the body of a patient, proximal extremity 36a thereof is outside of the body. First and second tubular members in the form of first and second guide tubes 46 and 47 extend through distal extremity 36b of the torque tube 36 to a guide means or housing 48 mounted on distal extremity 36b. First and second guide tubes 46 and 47 are each made from any suitable material such as stainless steel and have respective first and second lumens 51 and 52 extending longitudinally therethrough. The proximal portions of the guide tubes 46 and 47 are secured to the distal end of cartridge housing 41 atop torque tube 36 so that lumens 51 and 52 communicate with recess 43 in cartridge housing 41. Guide tubes 46 and 47 enter passageway 38 through a hole 53 formed in proximal extremity 36a and extend side-by-side along the top portion of distal extremity 36b.

Guide housing 48 is formed with an annular barb 49 on the proximal end thereof which is cooperatively coupled by being press fit into the distal end of passageway 38. Guide housing 48 can be further secured to torque tube 36 by any suitable means such as an adhesive (not shown). Guide tubes 46 and 47 each curve downwardly as they extend through guide housing 48 and terminate at respective ports 54 opening through the bottom of the guide housing. The guide housing 48 is made from any suitable transparent material having a refractive index in the range of about 1.3 to about 1.7. As more particularly described in copending patent application Ser. No. 08/835956 filed Apr. 11, 1997, a suitable material for guide housing 48 is a transparent polymer. Guide housing 48 has a rounded and upturned distal end 61.

At least one and as shown in FIG. 3 first and second stylets 62 and 63 are slidably disposed within first and second lumens 51 and 52 of first and second guide tubes 46 and 47. Stylet 62 has a radio frequency needle electrode 66 made from any suitable conductive material such as a nickel titanium alloy. A layer of non-conductive material in the form of first insulating sleeve 67 is coaxially mounted on needle electrode 66. More specifically, sleeve 67 is slidably disposed on needle electrode 66. Electrode 66 has proximal and distal extremities 66a and 66b and sleeve 67 has proximal and distal extremities 67a and 67b. Second stylet 63 is substantially identical to first stylet 62 and includes a second radio frequency needle electrode 68 having a second insulating sleeve 69 slidably mounted thereon. Electrode 68 has proximal and distal extremities 68a and 68b and sleeve 69 has proximal and distal extremities 69a and 69b. The distal ends of first and second needle electrodes 66 and 68 are pointed and the distal ends of first and second insulating sleeve 67 and 69 are tapered to facilitate insertion of the distal extremities of first and second stylets 62 and 63 through the urethral wall into the tissue of the prostate.

Figure 2:
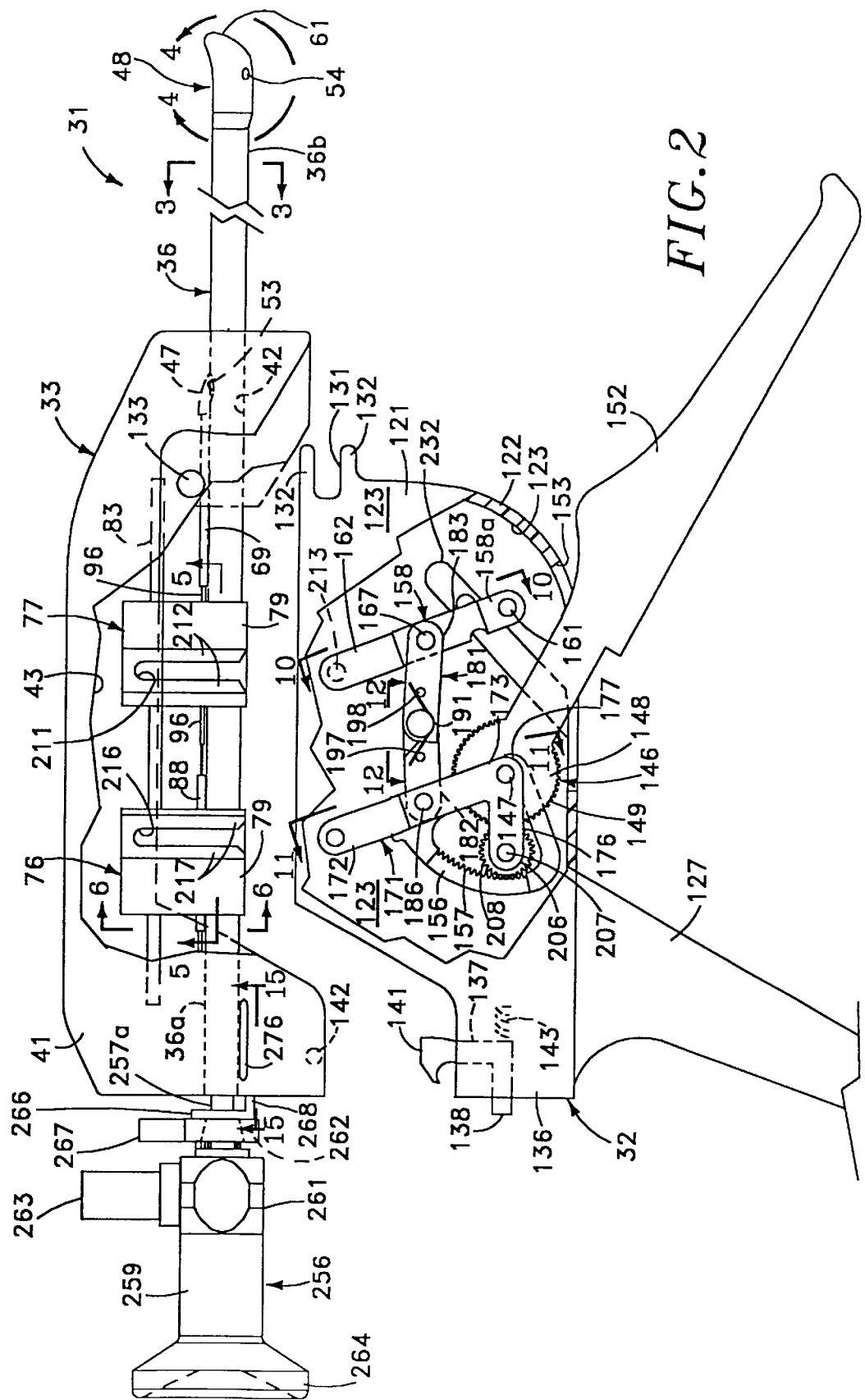
FIG. 2 is a side elevational view of the transurethral needle ablation device of FIG. 1 with the cartridge separated from the handle housing.

First and second slides 76 and 77 are carried by cartridge housing 41 within recess 43 for moving first and second stylets 62 and 63 longitudinally within first and second guide tubes 46 and 47. Slides 76 and 77 are each made from a block 78 formed from any suitable material such as nylon (see FIGS. 5 and 6). Blocks 78 each have first and second opposite, planar surfaces 79 and are each provided with top and bottom recesses 81 and 82 so as to be substantially H-shaped in conformation, as shown in FIG. 6 with respect to needle slide 76. First or needle slide 76 and second or insulation slide 77 slidably sit on proximal extremity 36a of torque tube 36. More specifically, torque tube 36 extends through lower recess 82 of the slides 76 and 77. A cylindrical guide rod 83 serves to retain the slides 76 and 77 on torque tube 36. Guide rod 83 is made form any suitable material such as stainless steel. The guide rod 83 extends above torque tube 36 in a direction parallel to longitudinal axis 37 through recess 43 of cartridge housing 41. Rod 83 is secured at each end to cartridge housing 41 by any suitable means such as being captivated by features of the housing 41 (not shown). The rod 83 sits within upper recess 81 of each of the slides 76 and 77. Needle slide 76 is disposed proximal of sleeve slide 77 as shown in FIG. 2.

Means is provided for securing the proximal extremities of first and second needle electrodes 66 and 68 to needle slide 76. In this regard, each of blocks 78 is formed with a first or left groove 86 and a second or right groove 87 extending longitudinally through the blocks at the top of lower recess 82 (see FIG. 5). A needle connector tube 88 is press fit into each of grooves 86 and 87. Each of tubes 88 has an enlarged central portion 88a which seats within a transverse groove 89 extending across the grooves 86 and 87 for precluding longitudinal movement of the connector tube 88 relative to block 78. The proximal ends of first and second needle electrodes 66 and 68 extend through respective connector tubes 88 and are secured thereto by crimps 92 formed in each of the connector tubes 88. Tubes 88 can be further secured within grooves 86 and 87 by any suitable means such as an adhesive (not shown).

The proximal ends of first and second insulating sleeves 67 and 68 are secured to the underside of sleeve slide 77 in a similar manner (see FIG. 5). First and second sleeve connector tubes 96 are press fit within left and right grooves 86 and 87 of the sleeve slide 77. An adhesive (not shown) can be provided for further securing sleeve connector tubes 96 within the grooves 86 and 87. Each of tubes 96 has an enlarged disk 96a provided thereon which seats within an enlarged recess 97 provided in the respective groove 86 or 87 of sleeve slide 77. The proximal extremities 67a and 69a of first and second insulating sleeves 67 and 69 slip over the distal ends of sleeve connector tubes 96 with an interference fit and can be further secured thereto by an adhesive (not shown) or any other suitable means. Proximal extremities 66a and 68a of first and second needle electrodes 66 and 68 extend through respective connector tubes 96.

The proximal ends of first and second needle electrodes 66 and 68 are electrically connected to a cable 106 extending from cartridge housing 41 to a pin connector 107. Cable 106 and pin connector 107 are shown only in FIG. 1. Temperature sensing means in the form of temperature sensors 108 are carried by the distal ends of first and second insulating sleeves 67 and 69. Sensors 108 are each located approximately 2.2 millimeters from the distal ends of sleeves 67 and 69. Electrical leads (not shown) extend from sensors 108 through cable 106 to connector 107. A suitable radio frequency and controller 111, such as the type described in co-pending patent application Ser. No. 08/833,982 filed Apr. 11, 1997, is connected to device 31 by means of connector 107 (see FIG. 1).

Handle assembly 32 has a housing 121 made from any suitable material such as stainless steel. Housing 121 is formed from opposite first and second shells 122, one of which is shown in FIG. 1 and each of which includes a side wall 123. Shells 122 and spaced-apart side walls 123 thereof define an internal cavity 126 within housing 121. A handle 127 extends downwardly from the rear of housing 121 at an acute angle relative to longitudinal axis 37.

Cooperative mating means is carried by cartridge 33 and handle assembly 32 for removably mounting the cartridge on housing 121 (see FIGS. 1 and 2). In this regard, a pair of transversely-aligned recesses 131 are provided at the top distal end of housing side walls 123. Each recess 131 is formed by a pair of spaced-apart arms 132 formed integral with the side walls 123. Each of such recesses is sized and shaped to slidably receive a button 133 extending from the side of cartridge housing 41. Buttons 133 are in transverse alignment on housing 41. The cooperative engagement of arms 132 about buttons 133 permits handle assembly 32 to pivot upwardly about the buttons until the tops of side walls 123 abut cartridge housing 41 as shown in FIG. 1. The bottom of cartridge housing 41 fully engages the top of housing 121 so as to cover internal cavity 126 in the housing 121. Needle and sleeve slides 76 and 77 depend into the internal cavity 126. Housing 121 includes a rear portion 136. A latch member 137 having a finger operable button 138 and a hook 141 is provided in rear portion 136 (see FIG. 2). Hook 141 extends upwardly from rear portion 136 and cooperatively engages a transversely-extending pin 142 accessible from the underside of cartridge housing 41. Latch member 137 and hook 141 thereof are urged rearwardly by a spring 143 provided in housing 121. In this manner, latch member 137 serves to lock cartridge 33 to handle assembly 32.

Figure 7:
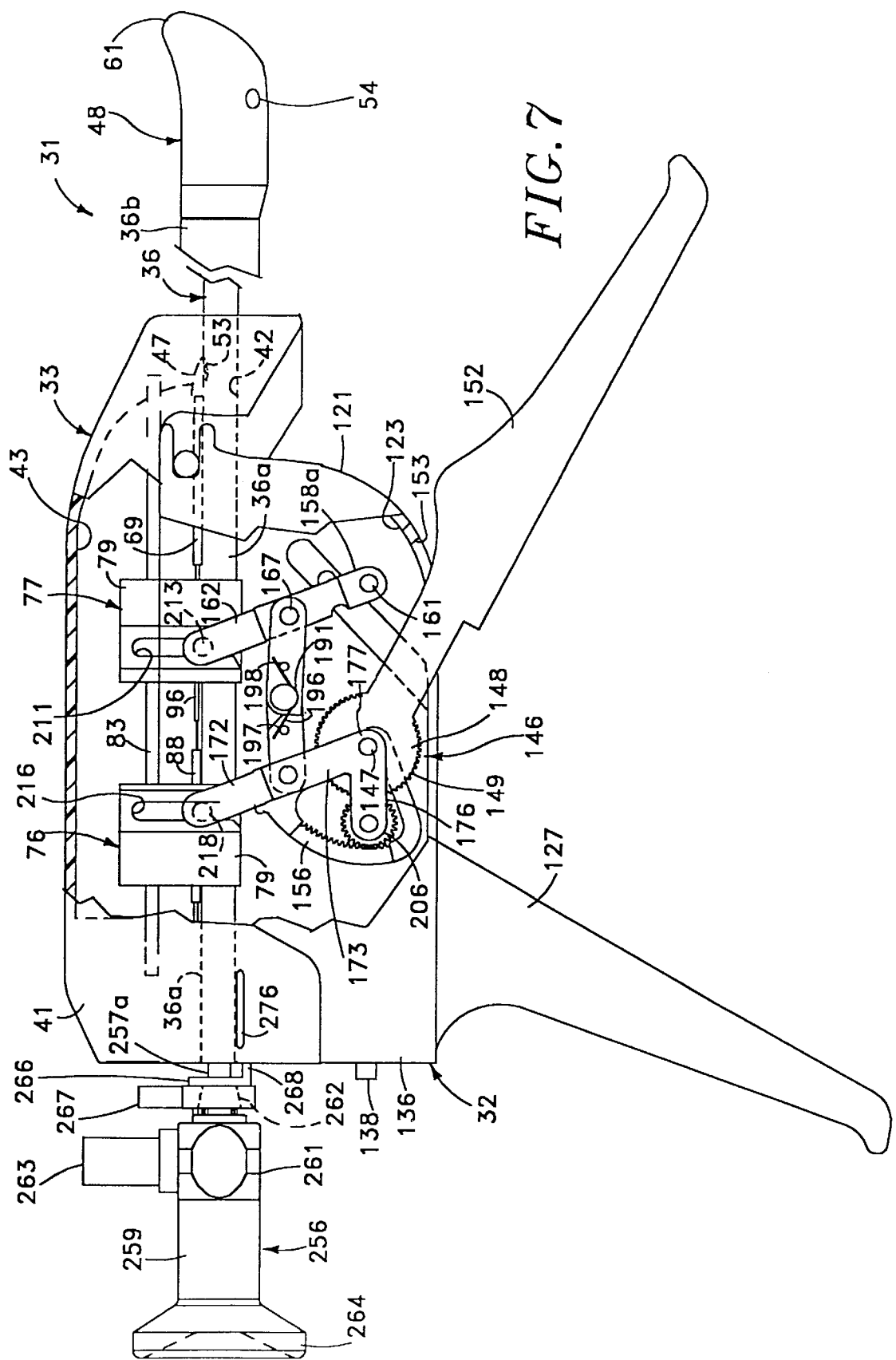
FIG. 7 is a side elevational view of the transurethral needle ablation device of FIG. 1, cut away to expose the interior of the device.

Hand operable means is carried by housing 121 and coupled to the proximal extremities of first and second stylets 62 and 63 for advancing and retracting the stylets 62 and 63 relative to guide housing 48. The hand operable means includes a planetary gear assembly 146 pivotally coupled to housing 121 by means of a pin 147 secured at each of its ends to side walls 123. Pin 147 extending transversely between the side walls 123 at right angles thereto. Planetary gear assembly 146 includes a first gear in the form of sun gear 148 rotatable about pin 147. Sun gear 148 has a plurality of teeth 149 extending radially outwardly and generally centered on a radius of approximately 0.75 inch. Finger actuable means in the form of elongate lever 152 is formed integral with sun gear 148 and extends out of internal cavity 126 through an opening 153 provided in housing 121. As shown in FIGS. 1, 2 and 7, lever 152 extends forwardly at an acute angle relative to longitudinal axis 37 when in its home position as in those figures.

A second gear in the form of ring gear 156 is included within planetary gear assembly 146. Ring gear 156 rotates above pin 147 relative to housing 121 and includes a plurality of teeth 157 extending radially inwardly toward pin 147. Teeth 157 are generally centered on a radius of approximately 1.25 inches. It is desirable that the ratio of the radii of ring gear 156 to sun gear 148 range from 1.5:1 to 3:1. Rotation of ring gear 156 in a counterclockwise direction in FIGS. 7–9 about pin 147 causes a first yoke member or sleeve yoke 158 to also pivot in a counterclockwise direction relative to housing 121. Sleeve yoke 158 has a first end portion or central leg 158a pivotally connected to a pin 161 secured at each of its ends to side walls 123 (see FIG. 10). Pin 161 extends transversely between the side walls 123 in a direction parallel to pin 147. Sleeve yoke 158 has a second end portion 158b formed from parallel, spaced-apart upstanding arms 162. A rigid, elongate link 163 serves to connect ring gear 156 to sleeve yoke 158. Link 163 extends generally in a direction parallel to longitudinal axis 37. A first connecting pin 166 serves to pivotally connect the proximal end of link 163 to ring gear 156 and a second connecting pin 167 serves to pivotally connect the distal end of link 163 to sleeve yoke 158.

A second yoke member in the form of needle yoke 171 made from any suitable material such as stainless steel is included in the deployment mechanism of handle assembly 32. As shown in FIG. 11, needle yoke 171 has a front profile which is generally H-shaped. The needle yoke 171 includes first or left and second or right spaced-apart arms 172 which extend upwardly and first or left and second or right spaced-apart legs 173 which extend downwardly. A leg extension 176 joins each leg 173 at an elbow 177 and extends upwardly from the leg 173 at an acute angle of approximately 60° (see FIGS. 7–9). Pin 147 extends from side walls 123 through each of elbows 177 to pivotally couple needle yoke 171 to housing 121. As shown in FIG. 11, sun gear 148 and ring gear 156 are pivotally coupled to pin 147 between legs 173 of the needle yoke 171.

Figure 8:
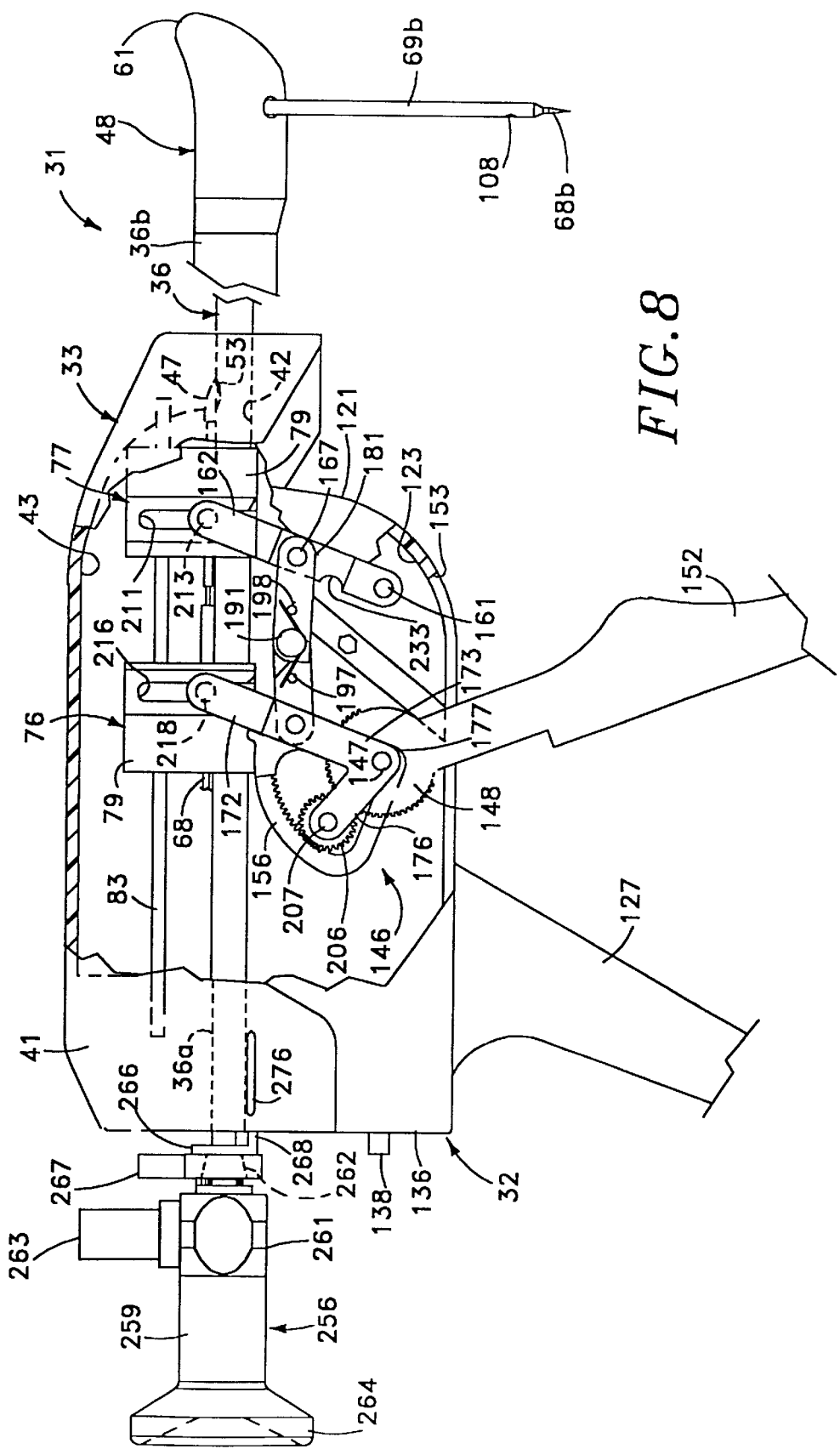
FIG. 8 is a side elevational view of the transurethral needle ablation device of FIG. 1, cut away similar to FIG. 7 and showing the device in another position.
Figure 9:
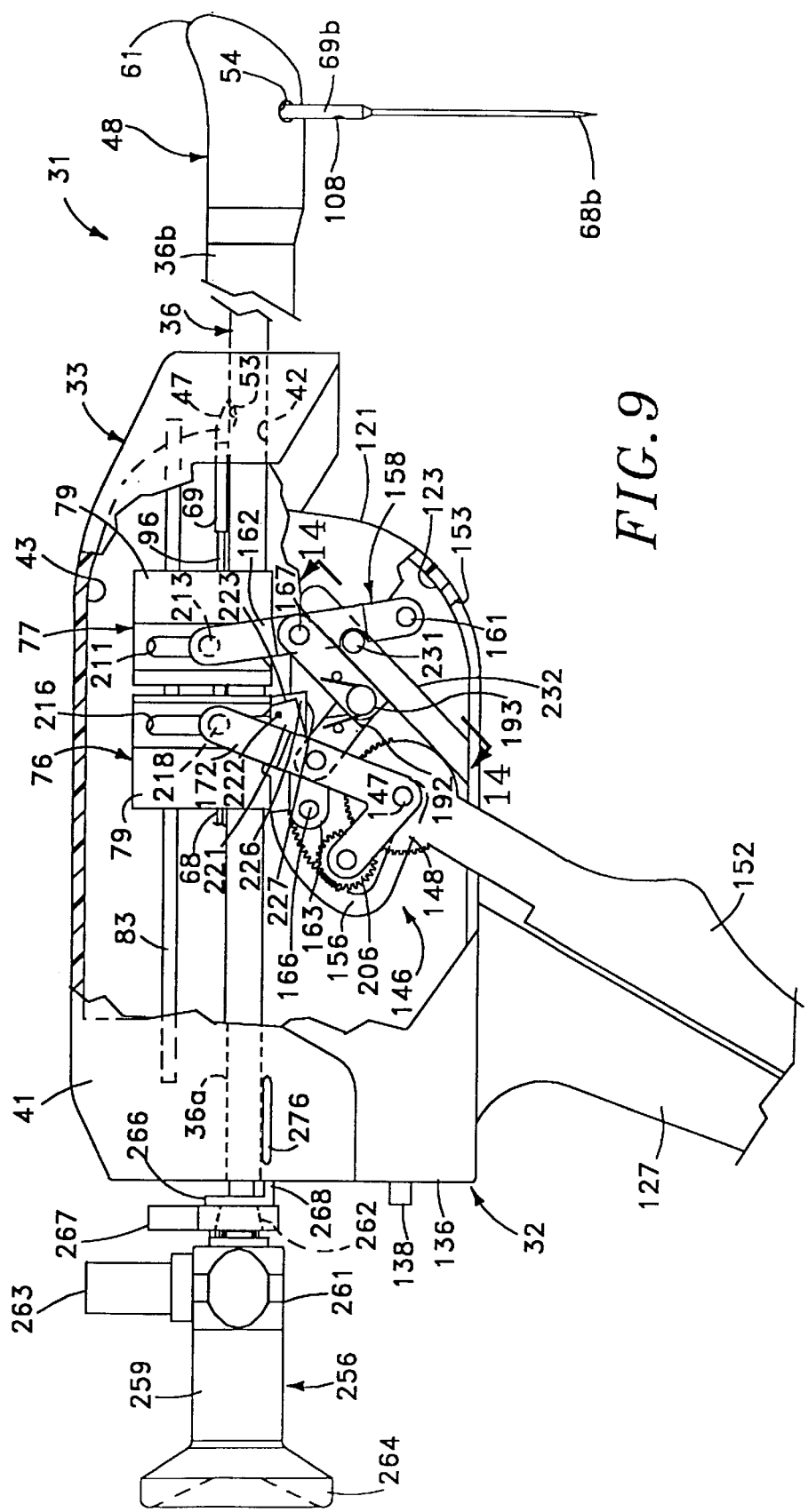
FIG. 9 is a side elevational view of the transurethral needle ablation device of FIG. 1, cut away similar to FIG. 7 and showing the device in a third position.

Sleeve and needle yokes 158 and 171 are coupled together by means of a buckleable link 181 (see FIGS. 7–9). Buckleable link 181 has first and second elongate link members 182 and 183. The proximal end of first link member 182 is pivotally coupled to left leg 173 of needle yoke 171 by means of transversely-extending pin 186, as shown in FIGS. 7–9 and 11. The distal end of second link member 183 is pivotally coupled to sleeve yoke 158 by means of pin 167, as shown in FIGS. 7–10. The distal end of the first link member 182 is pivotally coupled to the proximal end of the second link member 183 by means of a transversely-extending connecting pin 191, as shown in FIGS. 7–9 and 12–13. Link members 182 and 183 are restricted from pivoting upwardly over center relative to each other by the engagement of surface 192 of first link member 182 with surface 193 of second link member 183, as shown in FIGS. 13. However, the first and second link members 182 and 183 are free to pivot downwardly, as shown in FIG. 9, once connecting pin 191 has been urged over center. Thus, buckleable link 181 is movable between a first substantially straightened position in which link 181 is in an over center position, shown in FIGS. 7–8 and 13, and a second buckled or bent position, shown in FIG. 9. While in an over center condition, link 181 can support on axis loads of very high magnitude.

Means is carried by buckleable link 181 for urging first and second link members 182 and 183 to their substantially straightened position and includes torsion spring 196 which serves as a spring means. The spring 196 is concentrically mounted about connecting pin 191 and has a first end abutting a cylindrical retainer post 197 provided on first link member 182. Spring 196 has a second end abutting a cylindrical retainer post 198 provided on second link member 183.

A cylindrical third gear 206 is pivotally coupled between the ends of leg extensions 176 of needle yoke 171. A pin 207 is connected at each end to a leg extension 176 and extends through third gear 206 for permitting the gear 206 to rotate relative to needle yoke 171. Third gear 206 serves as the at least one planet gear of planetary gear assembly 146 and has a cylindrical surface formed by a plurality of teeth 208 which mesh with teeth 149 of sun gear 148 and teeth 157 of ring gear 156.

Means is included within handle assembly 32 and cartridge 33 for removably coupling ring gear 156 to the proximal extremities of first and second insulating sleeves 67 and 69 when the cartridge 33 is mounted atop handle assembly 32 in the manner described above. Such means includes sleeve yoke 158 and sleeve slide 77. As shown in FIGS. 2 and 5, sleeve slide 77 is provided with first and second transversely-aligned slots 211 which extend vertically on the opposite side surfaces 79 thereof. Each of the slots 211 is defined by first or proximal and second or distal spaced-apart ribs 212 formed on the surface 79. A cylindrical pin 213 extends transversely inwardly from the end of each arm 158b of sleeve yoke 158. The opposed pins 213 are cooperatively sized and shaped for upward and downward slidable disposition within slots 211.

Means is also included within transurethral needle ablation device 31 for coupling planet gear 206 to the proximal extremities of first and second needle electrodes 66 and 68. As can be seen from FIGS. 5 and 7, said means includes first and second slots 216 provided on the opposite side surfaces 79 of needle slide 76. Slots 216 are substantially similar to slots 211 and are each formed from first or proximal and second or distal vertically-disposed ribs 217 provided on surface 79. First and second transversely-extending pins 218 are provided on the upper ends of arms 172 of needle yoke 171. The opposed, cylindrical pins 218 are sized and shaped for upward and downward slidable disposition within slots 216.

Lever 152 is pivotable about pin 147 between a first or home position shown in FIGS. 7, through a second or intermediate position shown in FIG. 8 to a third or fully actuated position shown in FIG. 9. The lever 152 travels through an angle of approximately 70° between its home position of FIG. 7 and its fully actuated position of FIG. 9. It is desirable to minimize the aggregate angular travel of lever 152 for ease of gripping. However, reductions in such angular travel result in sacrifices to the mechanical advantage of planetary gear assembly 146. As shown in FIG. 8, movement of lever 152 from its first position to its intermediate position results in the distal ends of needle electrodes 66 and 68 and insulating sleeves 67 and 69 extending simultaneously from ports 54 of guide housing 48 to a fully extended position in which the distal ends of stylets 62 and 63 extend sidewise relative to longitudinal axis 37. More specifically, buckleable link 181 acts as a rigid link between sleeve and needle yokes 158 and 171 precluding counter-clockwise rotation of the sleeve yoke 158 about pin 161 during such pivoting of lever 152 to its intermediate position. Since ring gear 156 is rigidly coupled to the sleeve yoke 158 by means of link 163, needle yoke 171 and ring gear 156 are forced to move in unison about pin 147. The rotatable force acting on ring gear 156 and needle yoke 171 results from the non-rotatable engagement of the teeth 208 of planet gear 206 with the teeth 146 of sun gear 148 and with the teeth 157 of the ring gear 156. As can be seen, planet gear 206 thus serves to transmit rotational torque from lever 152 to ring gear 156. Sleeve and needle yoke 71 move in parallel during movement of lever 152 from its home position to its intermediate position, link 181 precluding premature retraction of insulating sleeves 67 and 69 during such deployment of the needle electrodes 66 and 68 and the insulating sleeves 67 and 69.

Transurethral needle ablation device 31 permits the operating physician to adjust the distance by which first and second needle electrodes 66 and 68 extend from guide housing 48. A stop block 221 is carried by housing 121 and serves as means for determining the distance which first and second needle electrodes 66 and 68 extend from guide housing 48. Block 221, as shown only in FIG. 9 for simplicity, is pivotably mounted inside housing 121 by means of a pin 222, shown in FIGS. 1 and 9, extending transversely through the block 221 and side walls 123 at right angles to the side walls. Block 221 has a plurality of four side faces 223 extending parallel to pin 222 for engaging needle yoke 171. A pointer knob 224 is mounted on the portion of pin 222 extending outside side wall 123 and can be rotated about pin 222 toward one of the various needle extension lengths printed on the outside of housing 121 for selecting the desired face 223 on block 221 (see FIG. 1). Device 31 is shown as permitting needle electrodes 66 and 68 to be extended to distances of either 14, 17, 20 or 22 millimeters. Faces 223 are each spaced from the center of pin 222 a distance corresponding to the forward limit of travel for needle yoke 171 which relates to the needle extension length selected on the outside of the housing 121. Needle yoke 171 abuts the selected face 223 of stop block 221 and thus determines the amount by which needle electrodes 66 and 68 extend from guide housing 48.

Release means is carried by housing 121 for urging connecting pin 191 against the force of torsion spring 196 over center when lever 152 is moved to its second position shown in FIG. 8. Said release means originates from loads created by lever 152 and is in the form of a release block 226 pivotably coupled to housing 121 by means of pin 222. For simplicity, block 226 is shown only in FIG. 9. Release block 226 is disposed on pin 222 adjacent stop block 221 and is rotatable within housing 121 by means of pointer knob 224. Block 226 has a plurality of four planar faces 227 for engaging buckleable link 181. Faces 227 are each ramped so as to move connecting pin 191 downwardly over center as yolks 158 and 171 pivot clockwise under the force of lever 152. Faces 227 are appropriately spaced from the center of pin 222 and provided with the appropriate slope to accommodate the angle and disposition of link 181 within housing 121 as determined by the angular position of needle yolk 158 about pin 147. Corresponding faces 223 and 227 are generally spaced apart angularly about pin 222 by approximately 90°. Once buckleable link 181 has been so moved downwardly over center, it will pivot about pin 191 if a compressive longitudinal force is simultaneously exerted thereon. Sleeve yolk 158 is now permitted to rotate in a counterclockwise direction relative to needle yolk 158.

Movement of lever 152 from its intermediate position as shown in FIG. 8 to its fully actuated position shown in FIG. 9 results in the retraction of the distal extremities of first and second insulating sleeves 67 and 69 relative to the distal extremities of first and second needle electrodes 66 and 68 as shown in FIG. 9. A predetermined portion of the length of needle electrodes 66 and 68 is thus exposed. Since sleeve yoke 158 is now permitted by buckleable link 181 to rotate about pin 161 in a counterclockwise direction, further clockwise pivoting of lever 152 about pin 147 results in counterclockwise rotation of planet gear 206 under the force of teeth 149 of sun gear 148. Teeth 208 of the planet gear 206 engage teeth 151 of ring gear 156 and serve to pivot the ring gear in a counterclockwise direction about pin 147. Rigid link 163 forces sleeve yoke 158 in a rearward direction under the force of ring gear 156. Needle yoke 171 is retained in its forward position by the interengagement of sun gear 148 and planet gear 206 to thus cause first and second needle electrodes 66 and 68 to remain in their fully extended position during the retraction of first and second insulating sleeves 66 and 69.

A stop 231 engages sleeve yolk 158 to limit its counter-clockwise rotation about pin 161 and thus limit the retraction of insulating sleeves 67 and 69 to the desired extension of approximately six millimeters from guide housing 48 (see FIGS. 9 and 14). Stop 231 is secured to the end of a leaf spring 232 attached to the inside of side wall 123 by any suitable means such as screws (not shown).

Sleeve yolk 158 is provided with a notch 233 for retaining the sleeve yolk against stop 231. The stop 231 is deflected toward the side wall 123 to an out-of-the-way position by lever 152 when the lever 152 is returned to its home position. Thus, sleeve yolk 158 can pivot sufficiently rearwardly to allow first and second insulating sleeves 67 and 69 to retract fully into guide housing 48 when the lever 152 is in its home position. Stop 231 leaf spring 232 are shown in FIG. 14 in dashed lines when moved by lever 152 to their out-of-the-way positions.

Although planetary gear assembly 146 has been described as having only one planet gear therein, it should be appreciated that planetary gear assemblies may have more than one planet gear or other planetary gear arrangements and be within the scope of the present invention. For example, an alternative planetary gear assemblies (not shown) can be provided having a planet gear and an idler gear rotatably carried by a yoke member coupled to the proximal extremities of the insulating sleeves. In this arrangement, the sun gear is formed integral with lever 152 and engages the planet gear, which in turn engages the idler gear. The ring gear pivots about the same axis as the sun gear and engages the idler gear. The needle yoke member is rigidly coupled to the ring gear and is connected to the proximal extremities of the needle electrodes. A buckleable link similar to link 181 interconnects the needle and sleeve yoke members and permits the sleeve yoke member to pivot rearwardly to retract the insulating sleeves upon full actuation of the lever.

Cartridges 33 can be provided having first and second needle electrodes 66 and 68 of varying lengths. For example, one cartridge 33 can be provided having needle electrodes 66 and 68 which fully extend a distance of approximately 14 millimeters from the outer surface of guide housing 48. A second cartridge housing 33 can be provided having needle electrodes 66 and 68 which extend a distance of 22 millimeters from the outer surface of guide housing 48. Handle assembly 32 can accommodate cartridges 33 having such differently sized needle electrodes.

Transurethral needle ablation device 31 can be used with an optical viewing device such as scope 256 made by Storz. Scope 256, in general, includes an elongate optical element 257 having proximal and distal extremities 257*a* and 257*b*. Optical element 257 has a distal viewing face 258 and is provided with an axially-extending central rod lens concentrically surrounded by a plurality or bundle of light fibers enclosed by a protective rigid tubular sheath made from any suitable material such as stainless steel. These internal components of optical element 257 are shown collectively in cross-section in FIG. 3. Scope 256 has a proximal portion which includes lens housing 259 interconnected to proximal extremity 257*a* of optical element 257 by fitting 261. The fitting 251 is formed with a distally projecting coupling extension 262 and is further provided with a light post 263 for permitting a suitable light source to be connected to the bundle of optical light fibers carried within optical element 257. Lens housing 258 has an eyepiece 264 at the proximal end thereof.

Means is carried by cartridge 33 for coupling proximal extremity 257*a* of optical element 257 to the proximal extremity 36*a* of torque tube 36 so that distal extremity 257*b* of the optical element is in the vicinity of distal extremity 36*b* of the torque tube (see FIGS. 1, 15 and 16). In this regard, cartridge 33 has a cylindrical connector 266 with a recess in its proximal end for receiving coupling extension 262 of scope 256. A knob 267 is rotatably carried by connector 266 for locking coupling extension 262 to the connector 266. Connector 266 and knob 267 can each be made from plastic or any other suitable material. When scope 256 is so secured to connector 266, optical element 257 extends through passageway 38 of torque tube 36 below first and second guide tubes 46 and 47 (see FIG. 3). Additional cartridges 33 can also be provided for use with other optical viewing devices or scopes.

As shown in FIGS. 1, 15 and 16, a plate-like bridge 268 is formed integral with connector 266 and extends distally therefrom. Bridge 268 is slidably received within a longitudinal recess 269 provided in cartridge housing 41. Means is included within cartridge 33 for sliding bridge 268 forwardly and rearwardly within recess 269 and includes a plate-like slide 276 carried within a transverse recess 277 provided in cartridge housing 41 above longitudinal recess 269. Slide 276 is made from any suitable material such as plastic and has a first or left end portion 276*a* and a second or right end portion 276*b*. The slide 276 is movable within recess 277 between a first position shown in FIG. 15, in which right end portion 276*b* extends outwardly from the right side of cartridge housing 41, and a second position shown in FIG. 16, in which left end portion 276*a* extends from the left side of cartridge housing 41.

A diagonal slot 278 extends through the opposite planar surfaces of slide 276 between left and right end portions 276*a* and 276*b* of the slide 276. Transverse recess 277 communicates with longitudinal recess 269 so that slide 276 extends across the top surface of bridge 268. A guide pin 281 extends upwardly from bridge 268 for travel within slot 278. As can be seen in FIGS. 15 and 16, transverse movement of slide 276 from its right position shown in FIG. 15 to its left position shown in FIG. 16 results in guide pin 281 being moved rearwardly relative to cartridge housing 41 and thus optical element 257 being slid proximally within passageway 38. Conversely, movement of slide 276 from its left position shown in FIG. 16 to its right position shown in FIG. 15 results in optical element 257 being moved distally within passageway 38.

Guide housing 48 is provided with a bore 286 extending longitudinally therethrough for receiving distal extremity 257*b* of optical element 257 (see FIG. 4). Bore 286 communicates with passageway 38 of torque tube 36 and has an opening 287 at the distal end of guide housing 48. When scope 256 is moved to its forward or distalmost position relative to cartridge 33 by means of slide 276, viewing face 258 of optical element 257 is disposed at opening 287 for providing a field of view extending forwardly of transurethral needle ablation device 31. When scope 256 is moved rearwardly to its proximalmost position relative to cartridge 33, viewing face 258 is disposed within transparent guide housing 48 at a position proximal of ports 54 for permitting viewing through transparent guide housing 48 of first and second stylets 62 and 63 as they extend outwardly from ports 54. Viewing face 258 is shown in its forward position by reference numeral 288 in FIG. 3 and in its rearward position by reference numeral 289 in FIG. 3.

Transurethral needle ablation device 31 has means which includes fitting 291 for permitting a saline or other suitable flushing fluid to be introduced through opening 287 for providing a clear field of view for scope 256. Fitting 291, shown only in FIG. 1 for simplicity, communicates with passageway 38 at proximal extremity 36*a* of torque tube 36. Suitable seals (not shown) are provided in passageway 38 for precluding fluids from leaking from the opening at the proximal end of the passageway where scope 256 enters torque tube 36.

In operation and use, transurethral needle ablation device 31 can be utilized for performing a procedure of the type described in detail in copending U.S. patent application Ser. No. 08/701,887 filed Aug. 23, 1996 and/or copending U.S.

patent application Ser. No. 08/833,982 filed Apr. 11, 1997 on a human male patient. The procedure can briefly be described as follows. The anatomy of interest in the male patient to undergo the procedure consists of a bladder which is provided with a base or bladder neck which empties into a urethra extending along a longitudinal axis. The urethra can be characterized as being comprised of two portions: a prostatic portion and a penile portion. The prostatic portion is surrounded by a prostate or prostate gland which is a glandular and fibromuscular organ lying immediately below the bladder. The penile portion of the urethra extends through the length of a penis. The urethra is provided with a urethral wall which extends through the length of the penis and through the prostate into the bladder. The prostate can be characterized as being comprised of five lobes: interior, posterior, median, right lateral and left lateral. The prostate is also provided with a verumontanum. The size of the prostate to be treated is determined by the operating physician in a conventional manner such as via rectal ultrasound.

Once the patient has been prepared, a conventional indifferent or grounding electrode 292 is placed on the patient's backside so that it is adherent thereto and makes good electrical contact with the skin of the patient. The indifferent electrode 292 permits monopolar ablation and is connected by an electrical cable (not shown) into control console and radio frequency generator 111. A conventional foot operated switch (not shown) can be connected by a cable into the console 111 for controlling the application of radio frequency power.

Transurethral needle ablation device 31 is prepared by selecting a suitable cartridge 33 and mounting it atop handle assembly 32. Different cartridges can be provided for treating the various lobes of the prostate. For example, cartridge 33 provides that distal extremities 62b and 63b of first and second stylets 62 and 63 extend from guide ports 54 of guide housing 48 at an angle of approximately 90° relative to longitudinal axis 37 (see FIGS. 7–9). Stylets 62 and 63, when viewed from the front of guide housing 48, diverge or splay at an angle of approximately 40° relative to each other. Such a guide housing 48 is particularly suited for treating the lateral lobes of the prostate. Alternatively, if it is desired to treat the median lobe of the prostate, a cartridge 33 can be provided with a guide housing 48 which directs first and second stylets 62 and 63 forwardly at an acute angle relative to longitudinal axis 37.

Cartridge 33 is mounted to handle 32 by sliding each set of arms 32 provided on housing 121 about respective buttons 133 formed on the cartridge 33. Once the transversely aligned buttons 133 are disposed within recesses 131, handle assembly 32 is pivoted upwardly until hook 141 of latch member 137 engages and locks about pin 142 of cartridge 33. Knob 224 is rotated until it points to the needle length corresponding to cartridge 33.

Scope 256 is now mounted to cartridge 33 of device 31. As discussed above, distal extremity 257b of scope optical element 257 is introduced through connector 266 into passageway 38 and slid therethrough until coupling extension 262 engages the connector 266. Scope 256 is locked to connector 266 and thus cartridge 33 by rotation of knob 267 about longitudinal axis 37. During introduction of device 31 into the urethra, scope 256 is placed in its forward position by means of slide 276 so that viewing face 258 is disposed at opening 287.

A suitable light source is connected to light post 263 of scope 256 and radio frequency generator and controller 111 is connected to device 31 by means of connector 107. A source of a suitable flushing fluid such as a saline solution is coupled to fitting 291 to permit introduction of the saline solution through passageway 38 and opening 287 provided in guide housing 48 during the procedure.

Torque tube 36 is adapted for insertion into a natural body opening such as the urethra. Prior to insertion, the operating physician introduces an anesthetic such as Lidocaine into the urethra by means of a needleless syringe and coats torque tube 36 with an anesthetic. The operating physician then positions device 31 so that handle 127 extends downwardly and inserts guide housing 48 into the urethra. The upturned distal end 61 of the guide housing 48 facilitates insertion of torque tube 36 into the urethra and its passage therethrough. The relatively small diameter of torque 36 further facilitates the comfortable insertion of tube 36 into the urethra. Distal extremity 36b of torque tube 36 is advanced through the urethra until it is in the vicinity of the prostate. A steady flow of flushing fluid introduced into the urethra via passageway 38 facilitates viewing the urethra wall with scope 256 so that the operating physician can ascertain when guide housing 48 is in the desired registration with the prostate.

Transurethral needle ablation device 31 can now be utilized to perform a needle ablation procedure on the prostate. Slide 276 is moved to its left position shown in FIG. 16 to move scope 256 proximally relative to cartridge 33. Viewing face 258 of the scope 256 is now in its proximal position to permit viewing of first and second stylets 62 and 63 as they are directed outwardly from guide housing 48. Lever 152 is grasped by the fingers of the operating physician and pulled rearwardly from its home position shown in FIG. 7 through its intermediate position shown in FIG. 8 to its fully actuated position shown in FIG. 9. As discussed above, the distal extremities of needle electrodes 66 and 68 and insulating sleeves 67 and 69 coaxially mounted on the electrodes penetrate the urethral wall and extend into the tissue of the prostate as lever 152 is moved to its intermediate position. The amount of such extension corresponds to the needle extension length selected by pointer knob 224. In this regard, needle yoke 171 engages the selected face 223 of stop block 221 to limit the forward travel of yoke 171 in internal cavity 126. Further clockwise pivoting of lever 152 about pin 147 results in first and second insulating sleeves 67 and 69 partially retracting back into ports 54 so as to expose a predetermined length or portion of needle electrodes 66 and 68. Sleeves 67 and 69 extend a distance of approximately six millimeters from ports 54 when in their retracted position and thus remain extended through the urethral wall.

Once first and second stylets 62 and 63 have been so placed within the target prostatic tissue to be ablated, radio frequency energy is supplied by means of radio frequency generator and controller 111 in the manner described in copending patent application Ser. No. 08/701,887 filed Aug. 23, 1996 and/or copending U.S. patent application Ser. No. 08/833,982 filed Apr. 11, 1997. The radio frequency energy supplied to needle electrodes 66 and 68 is conducted through the tissue of the prostate to the return or indifferent electrode 292 provided on the outside of the patient when performing monopolar ablations. In this manner, lesions are created in the target volume of prostatic tissue in the vicinity of the exposed portions of needle electrodes 66 and 68. These lesions serve to shrink the size of the prostate. The thermocouples carried by first and second insulating sleeves 67 and 69 are disposed within the prostate and permit measuring of the temperature of the tissue being ablated. The information from the thermocouples can be utilized to be sure that the urethral wall is not damaged by the ablation procedure. Scope 256 permits the operating physician to view the urethral wall during the procedure. Scope 256 can be removed during the procedure to permit rapid draining of the bladder through passageway 38.

It should be appreciated that transurethral needle ablation device 31 can also be used for performing a bipolar ablation and be within the scope of the present invention. In such a procedure, radio frequency energy is supplied through one of needle electrodes 66 and 68 for conduction through the tissue to be ablated and returned through the other needle electrode. Radio frequency generator and controller 111 is capable of providing both monopolar and bipolar frequency outputs at relatively low power.

After the desired lesions have been created in the prostate by transurethral needle ablation device 31, the operating physician pivots lever 152 in a counterclockwise direction back to its home position to retract first and second styles 62 and 63 from the prostate into guide housing 48. During such pivoting of lever 152, the steps or movements within handle assembly 32 for deploying stylets 62 and 63 are reversed. Scope 256 can be utilized for viewing the retraction of stylets 62 and 63. Any further medicament such as an anesthetic can be introduced through torque tube passageway 38 by means of fitting 291. The operating physician can then withdraw transurethral needle ablation device 31 from the urethra.

Cartridge 33 is removed from handle assembly 32 by means of latch member 137. Handle assembly 32 can be autoclaved or otherwise sterilized for reuse.

Transurethral needle ablation device 31 is advantageous in many respects. Torque tube 36 and guide housing 48 are formed free of sharp surfaces which may irritate the urethral wall during insertion and use of transurethral needle ablation device 31. Scope 256 can be positioned in a forward position for viewing distally of device 31 during introduction of the device into the urethra. Slide 276 and connector 266 permit the scope 256 to be moved proximally so that stylets 62 and 63 can be visualized through the transparent guide housing as the stylets are deployed from ports 54. Guide housing 48 is free of external recesses for requiring such viewing. The folds of the urethral wall often drape into such recesses and obstruct the field of view of a scope having such recesses. Device 31 thus permits the insertion of stylets 62 and 63 through the urethral wall to be viewed from viewing face 258 of scope 256 without obstruction by the folds of the urethral wall.

Transurethral needle ablation device 31 utilizes a single-handed deployment mechanism in the form of lever 152. The operating physician is free to use his or her other hand during deployment and actuation of device 31. The full deployment of needle electrodes 66 and 68 and insulating sleeves 67 and 69 and the subsequent partial retraction of the insulating sleeves is accomplished in a single stroke of lever 152. The penetration distance of needle electrodes 66 and 68 and the operational deployment distance of insulating sleeves 67 and 69 is set once pointer knob 224 has been positioned on housing 121 to the desired extension length. Thus, the operating physician can be assured that stylets 62 and 63 are properly deployed once sleeve 152 has been fully pivoted relative to housing 121. The actuation force exerted on lever 152 by the operating physician is relatively constant and no unbalanced loads are transmitted to the patient during operation of the device 31.

Planetary gear assembly 146 permits a handle assembly 132 which is relatively simple in design and operation. Assembly 146 has relatively few parts and is supported by a single pin 147 extending between side walls 123 of housing 121. In addition, the assembly 146 ensures that the components of the deployment and retraction mechanism of stylets 62 and 63 are constantly in mesh. As a result, none of such components become unlatched or disconnected during use so as to risk improper deployment or withdrawal of needle electrodes 66 and 68 or insulating sleeves 67 and 69 during the procedure. Return of lever 152 to its home position after the procedure ensures that needle electrodes 66 and 68 and insulating sleeves 67 and 69 have been returned to their fully retracted positions with transurethral needle ablation device 31. Assembly 146 also causes needle electrodes 66 and 68 and insulating sleeves 67 and 69 to deploy simultaneously regardless of the loads on either of them.

Planetary gear assembly 146 provides a mechanical advantage during movement of lever 152 from its intermediate position of FIG. 8 to its fully actuated position of FIG. 9 to partially retract insulating sleeves 67 and 69. This mechanical advantage compensates for the greater forces required during retraction of sleeves 67 and 69 relative to the forces required for deployment of needle electrodes 66 and 68 and insulating sleeves 67 and 69. An approximate two to one mechanical advantage is provided on such retraction stroke due to the diameter of sun gear 148 being approximately one-half of the diameter of ring gear 156.

Although handle assembly 32 has been described as being constructed of components made of stainless steel so as to permit its sterilization and reuse, it should be appreciated that a disposable handle assembly made from plastic or other suitable materials can be provided and be within the scope of the present invention.

From the foregoing, it can be seen that a transurethral needle ablation device having a reusable handle assembly for controlling the deployment of one or more stylets has been provided. The stylet is contained in a cartridge which can be removably mounted on the handle assembly and includes a radio frequency electrode and an insulating sleeve coaxially disposed about the radio frequency electrode. The cartridge permits a scope to be removably coupled thereto. The scope can be moved longitudinally between a forward position for viewing distally of the device during its introduction into the body and a rearward position for viewing the stylet as it is deployed from the device. The handle assembly has relatively few parts and the deployment components of the handle assembly are constantly engaged to ensure proper deployment and retraction of the stylet during the procedure. The deployment components include a planetary gear assembly.

What is claimed is:

1. A medical probe device for the treatment by radio frequency ablation of a target volume in tissue of a prostate of a human male having a bladder with a base and a penis with a urethra therein formed by a urethral wall extending into the base of the bladder along a longitudinal axis with the tissue of the prostate surrounding the urethra near the base of the bladder comprising an elongate probe member having proximal and distal extremities and a longitudinal axis and having a passageway therein extending from the proximal extremity to the distal extremity along the longitudinal axis, the elongate probe member being sized to be able to enter the urethra and having a length so that when the distal extremity is disposed in the vicinity of the prostate the proximal extremity is outside of the urethra, a stylet mounted in the passageway of the elongate probe member and having a distal extremity, a handle coupled to the proximal extremity of the elongate probe member and extending in a direction which is substantially off-axis with respect to said longitudinal axis, finger actuatable means carried by the handle and connected to the stylet for causing advancement of the stylet through the passageway, the distal extremity of the elongate probe member being in communication with the passageway and the distal extremity of the stylet being advanceable out of the passageway sidewise in said same direction into the tissue of the prostate.

2. A device as in claim 1 wherein the stylet includes a conductive electrode.

3. A device as in claim 2 wherein the conductive electrode has a distal portion, a layer of insulating material extending around the conductive electrode but exposing the distal portion.

4. A device as in claim 3 wherein the conductive electrode is a radio frequency electrode.

5. A device as in claim 2 further comprising a radio frequency generator coupled to the stylet for supplying radio frequency energy to the conductive electrode, a return electrode electrically coupled to the radio frequency generator and in contact with the body.

6. A device as in claim 5 wherein the return electrode is a grounding electrode.

7. A device as in claim 1 further comprising guide means carried by the distal extremity of the elongate probe member and cooperatively coupled into the passageway for directing the distal extremity of the stylet in said direction.

8. A device as in claim 7 wherein the guide means includes a curved surface for directing the distal extremity of the stylet in said direction.

9. A device as in claim 1 further comprising an optical viewing device mounted in the elongate probe member and having a distal extremity positioned in the distal extremity of the elongate probe member and having a field of view which permits viewing the distal extremity of the stylet as it is advanced out of the passageway in said direction through the urethral wall into the tissue of the prostate.

10. A device as in claim 9 further comprising means for moving the optical viewing device from a first longitudinal position for viewing forward of the elongate probe member to a second longitudinal position for viewing the distal extremity of the stylet extending in said direction.

11. A disposable cartridge for use with a separate reusable handle assembly having a top portion to treat a prostate of a human male having a bladder with a base and a penis with a urethra therein formed by a urethral wall extending from the base of the bladder through the prostate and the penis along a longitudinal axis with the prostate having prostatic tissue surrounding the urethral wall near the base of the bladder, the cartridge comprising an elongate probe member having proximal and distal extremities and extending along a longitudinal axis and having a passageway extending from the proximal extremity to the distal extremity, the distal extremity of the elongate probe member being free of sharp surfaces so as to facilitate insertion of the elongate probe member into the urethra free of a separate sheath, the elongate probe member having a length so that when the distal extremity is in the urethra in the vicinity of the prostate the proximal extremity is outside of the body, a housing mounted on the proximal extremity of the elongate probe member, a radio frequency electrode having proximal and distal portions slidably disposed in the passageway and an insulating sleeve having proximal and distal portions slidably extending around the radio frequency electrode but capable of exposing the distal portion of the radio frequency electrode, the radio frequency electrode and the insulating sleeve being integrated with the elongate probe member and the housing, first and second slide members carried within the housing for slidable longitudinal movement therein, the proximal portion of the radio frequency electrode being coupled to the first slide member and the proximal portion of the insulating sleeve being coupled to the second slide member, the housing having a bottom portion provided with at least one opening for accessing the first and second slide members within the housing and means carried by the housing adapted to removeably engage the top portion of the reusable handle assembly for securing the housing to the reusable handle assembly and causing the removable handle assembly to engage the first and second slide members.

12. A cartridge as in claim 11 wherein the first and second slide members are slidably mounted on the proximal extremity of the elongate probe member.

13. A cartridge as in claim 11 further comprising a second radio frequency electrode slidably disposed in the passageway and having a distal portion, a second insulating sleeve extending around the second radio frequency electrode but exposing the distal portion.

14. A cartridge as in claim 11 further comprising a guide housing mounted on the distal extremity of the elongate probe member for directing the radio frequency electrode and the insulating sleeve sidewise of the longitudinal axis as they are moved distally in the passageway.

15. A cartridge as in claim 11 further comprising means carried by the housing for mounting an optical viewing device in the passageway.

16. A cartridge as in claim 15 wherein the means for mounting the optical viewing device in the passageway includes means for moving the optical viewing device from a first longitudinal position for viewing forward of the elongate probe member to a second longitudinal position for viewing the radio frequency electrode and the insulating sleeve extending from the distal extremity of the elongate probe member.

17. A cartridge for use with a separate reusable handle assembly to treat the prostate of a human male having a urethra therein, the cartridge comprising a housing, a radio frequency electrode having proximal and distal portions slidably coupled to said housing, an insulating sleeve having proximal and distal portions extending around the radio frequency electrode but exposing the distal portion of the electrode, means secured to said housing for inserting at least the distal portions of the electrode and sleeve directly into the urethra free of a separate sheath, first and second slide members carried within the housing, the proximal portion of the electrode being coupled to the first slide member and the proximal portion of the sleeve being coupled to the second slide member, the housing having a bottom portion provided with at least one open for permitting access to the first and second slide members and coupling means carried by the housing adapted for mounting the housing on the reusable handle assembly for securing the housing to the reusable handle assembly and causing the removable handle assembly to engage the first and second slide members.

18. A cartridge as in claim 17 wherein said inserting means includes an elongate probe member having proximal and distal extremities, extending along a longitudinal axis and having a passageway therein extending from the proximal extremity to the distal extremity along the longitudinal axis, the radio frequency electrode and insulating sleeve being disposed in said passageway, the distal extremity of the elongate probe member being free of sharp surfaces so as to facilitate insertion of the elongate probe member into the urethra.

* * * * *